United States Patent
Mori et al.

(10) Patent No.: US 12,365,857 B2
(45) Date of Patent: Jul. 22, 2025

(54) MULTI-LAYER CULTURE VESSEL OPERATION SYSTEM, MULTI-LAYER CULTURE VESSEL OPERATIONAL DEVICE, AND MULTI-LAYER CULTURE VESSEL OPERATION METHOD

(71) Applicant: Shikoku Instrumentation CO., LTD., Kagawa (JP)

(72) Inventors: Toshiaki Mori, Nakatado-gun (JP); Hideki Takeda, Nakatado-gun (JP); Yasufumi Mishima, Nakatado-gun (JP); Shoji Matsuoka, Nakatado-gun (JP)

(73) Assignee: SHIKOKU INSTRUMENTATION CO., LTD., Kagawa (JP)

( * ) Notice: Subject to any disclaimer, the term of this patent is extended or adjusted under 35 U.S.C. 154(b) by 1102 days.

(21) Appl. No.: 17/059,633

(22) PCT Filed: Dec. 21, 2018

(86) PCT No.: PCT/JP2018/047342
§ 371 (c)(1),
(2) Date: Nov. 30, 2020

(87) PCT Pub. No.: WO2019/230026
PCT Pub. Date: Dec. 5, 2019

(65) Prior Publication Data
US 2021/0222102 A1    Jul. 22, 2021

(30) Foreign Application Priority Data
May 30, 2018   (JP) ................. 2018-103792

(51) Int. Cl.
*C12M 1/00*   (2006.01)
*C12M 1/12*   (2006.01)
(Continued)

(52) U.S. Cl.
CPC ............ *C12M 23/04* (2013.01); *C12M 23/34* (2013.01); *C12M 23/44* (2013.01); *C12M 23/48* (2013.01);
(Continued)

(58) Field of Classification Search
USPC .......... 435/304.1, 304.2, 304.3, 305.1, 305.2
See application file for complete search history.

(56) References Cited

U.S. PATENT DOCUMENTS

2015/0017711 A1* 1/2015 Bennett ................. C12M 41/44
435/286.2
2018/0371394 A1* 12/2018 Ho ........................ C12M 29/24
2021/0207073 A1* 7/2021 Tanabe .................. C12M 41/46

FOREIGN PATENT DOCUMENTS

JP    3168263   *  6/2011
JP    3168263 U    6/2011
(Continued)

OTHER PUBLICATIONS

Thermo Scientific. "Thermo Scientific Nunc Automatic Cell Factory Manipulator System (ACFM)". from YouTube. 2014. http://www.youtube.com/watch?v=KiypKspvYuw (Year: 2014).*
(Continued)

*Primary Examiner* — Michael A Marcheschi
*Assistant Examiner* — Nathan G Esperon
(74) *Attorney, Agent, or Firm* — WHDA, LLP

(57) ABSTRACT

A multi-layer culture vessel operation system capable of easily performing a multi-layer culture vessel handling operation is provided. A multi-layer culture vessel operation system includes: a cart device 20 movable with a multi-layer culture vessel 30 mounted thereon; and an operational device 10 capable of holding and rotating the multi-layer culture vessel 30, wherein the cart device 20 includes: a cart 21 having wheels 22; and a fixing part 23 that is removably
(Continued)

mounted on the cart 21, and fixes the multi-layer culture vessel 30 to the cart, wherein the operational device 10 includes: a rotating portion 11 that holds the multi-layer culture vessel 30 and performs a rotation operation of rotating the multi-layer culture vessel 30 around a first rotation axis and/or a second rotation axis; a shaking portion 13 that holds the multi-layer culture vessel 30 and performs a shaking operation of shaking the multi-layer culture vessel 30 in a horizontal direction; and a control portion 15 that causes the shaking portion 13 to perform the shaking operation following the rotation operation by the rotating portion 11, without returning the multi-layer culture vessel 30 to the cart 21.

16 Claims, 10 Drawing Sheets

(51) Int. Cl.
*C12M 1/36* (2006.01)
*C12M 3/00* (2006.01)
*C12M 3/06* (2006.01)

(52) U.S. Cl.
CPC ............ *C12M 23/50* (2013.01); *C12M 23/52* (2013.01); *C12M 27/16* (2013.01); *C12M 41/48* (2013.01)

(56) References Cited

FOREIGN PATENT DOCUMENTS

| | | |
|---|---|---|
| JP | 2015505472 A | 2/2015 |
| JP | 2016-103984 A | 6/2016 |

OTHER PUBLICATIONS

Thermo Scientific. "Thermo Scientific Nunc Cell Factory Shaker". from YouTube. 2014. http://www.youtube.com/watch?v=elWCYvgKZ9M (Year: 2014).*
Thermo Scientific. "Data Sheet: Nunc Automated Cell Factory Manipulator". from Web Archive. 2021. https://web.archive.org/web/20210607132555/http://assets.thermofisher.com/TFS-Assets/BPD/Datasheets/nunc-automated-cell-factory-manipulator-data-sheet.pdf (Year: 2021).*
Shikoku Keizoku Kogyo Co., Ltd. "Multilayer culture inversion device" (machine translation). from Web Archive. 2015. https://web.archive.org/web/20150711144740/http://www.yonkei.co.jp:80/products/industrial/automation/inversion.html (Year: 2015).*
Ryan, John. "Subculturing Monolayer Cell Cultures". Corning Incorporated. Accessed Jan. 2, 2024. Available on Google in Nov. 1, 2016. (Year: 2016).*
Office Action dated May 19, 2023, issued in counterpart KR Application No. 10-2020-7032804, with English Translation. (20 pages).
"Multilayer incubator inversion device (4-layer 2D)", retrieved from the following website: Shikoku Instrumentation Co., Ltd. [online], <<http://www.yonkei.co.jp/products/industrial/automation/inversion.html>>, with Partial English Translation; Cited in KR Office Action dated May 19, 2023. (11 pages).
International Search Report dated Mar. 26, 2019, issued in counterpart International Application No. PCT/JP2018/047342 (2 pages).
International Preliminary Report on Patentability (Form PCT/IPEA/409) issued in counterpart International Application No. PCT/JP2018/047342 dated May 12, 2019 (7 pages).
2016-2017 Taitec-offline general catalogue, Taitec Corp., Sep. 1, 2015, p. 043; Cited in ISR dated Mar. 26, 2019 and IPRP dated May 12, 2019.
Multilayer incubator reversing device WAS-013, Shikoku Instrumentation Co., Ltd., Dec. 28, 2015, Online, http://www.yonkei.co.jp/products/industrial/automation/inversion.html; Cited in ISR dated Mar. 26, 2019 and IPRP dated May 12, 2019.

* cited by examiner

[Fig.1]
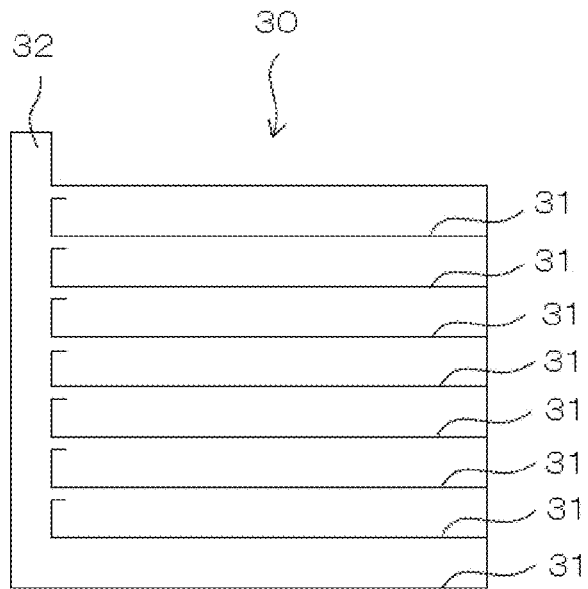
[Fig.2]
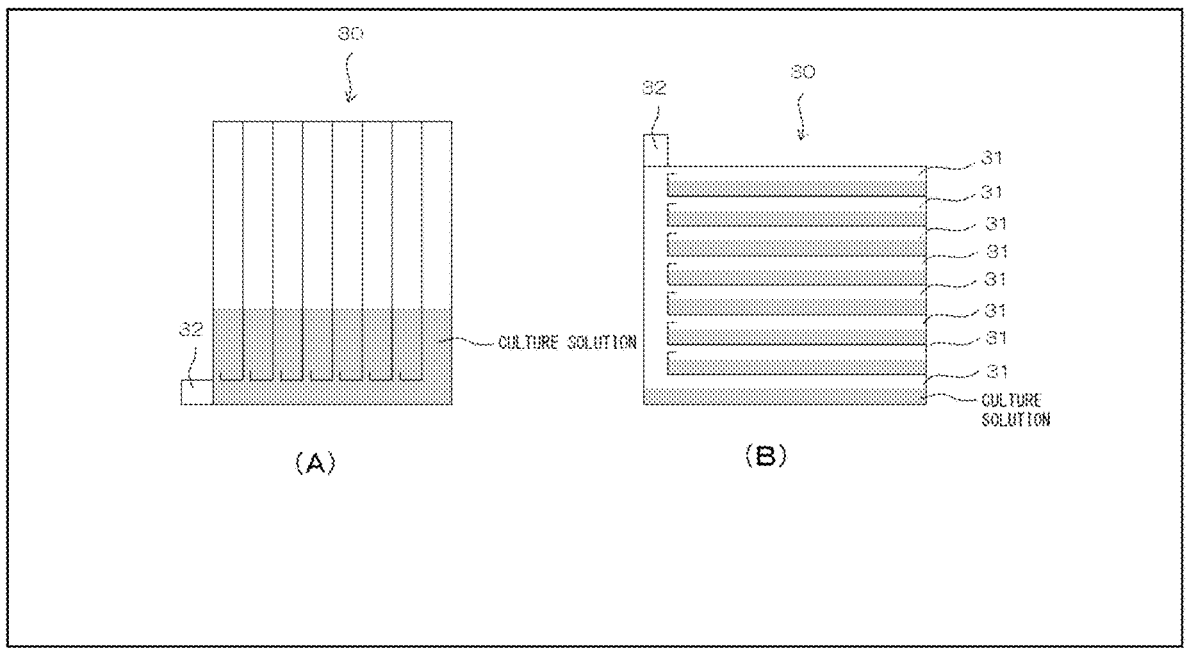

[Fig.3]
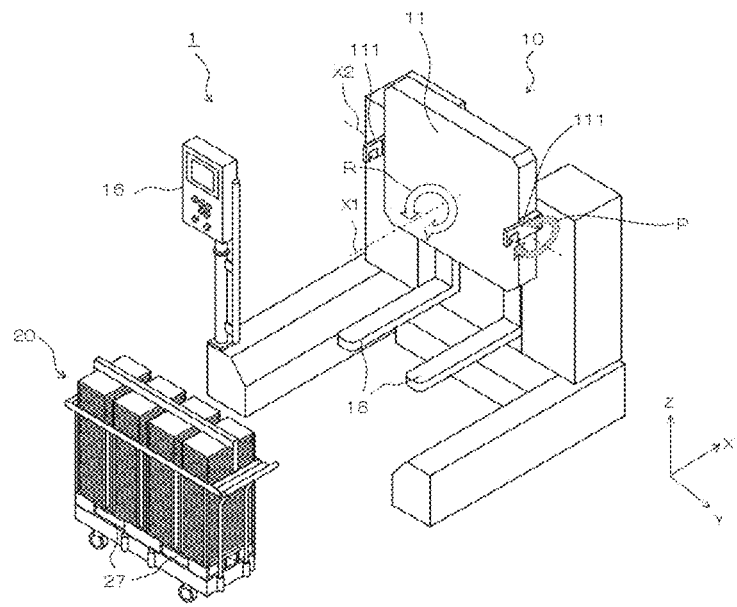
[Fig.4]
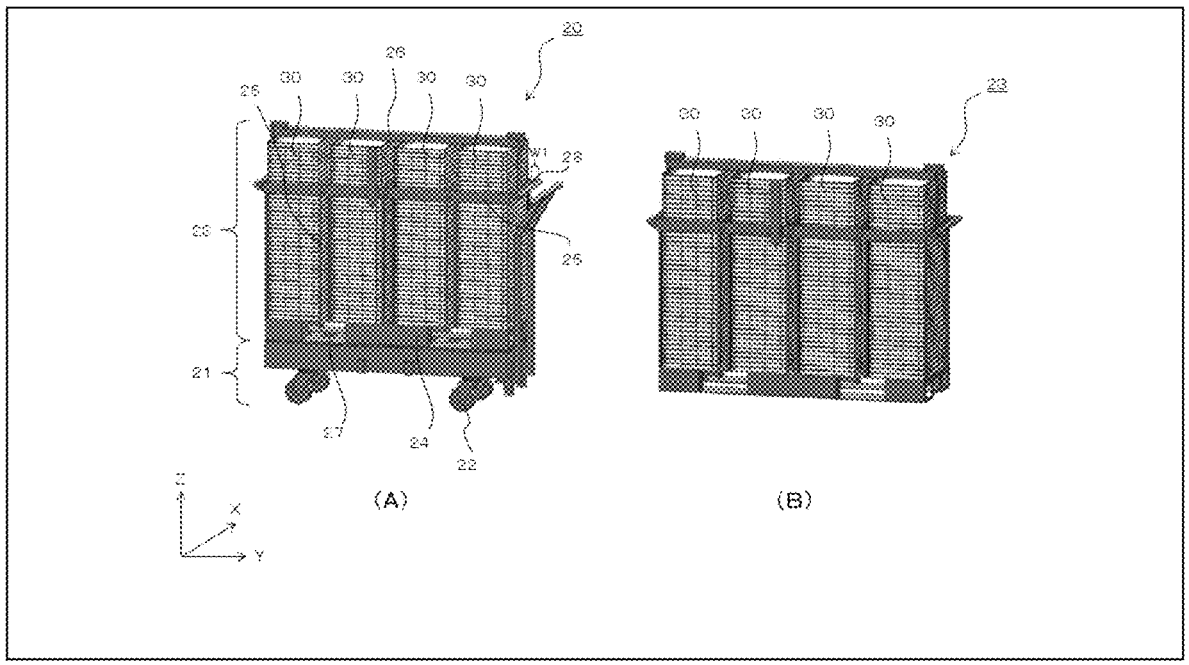
(A)          (B)

[Fig.5]
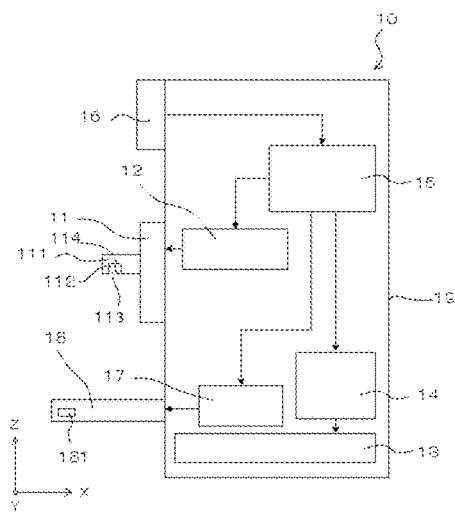
[Fig.6]
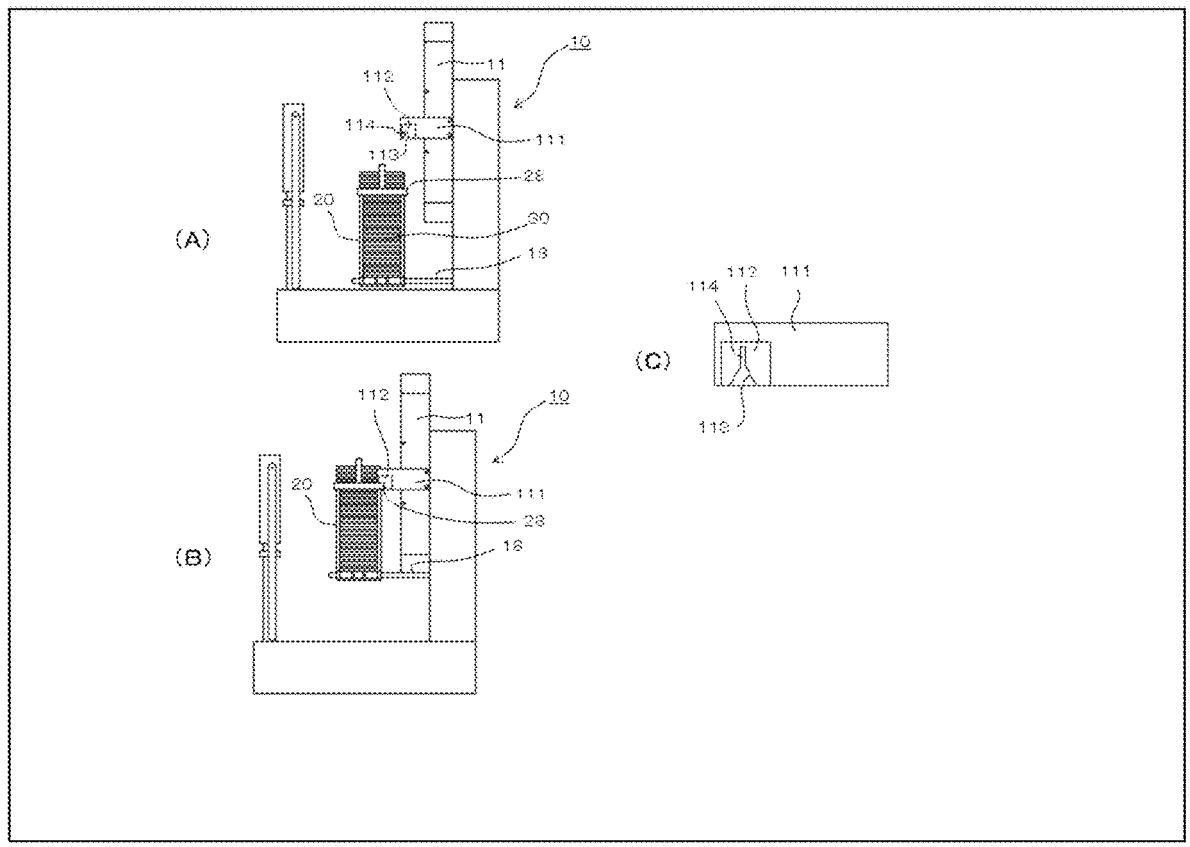

[Fig.7]
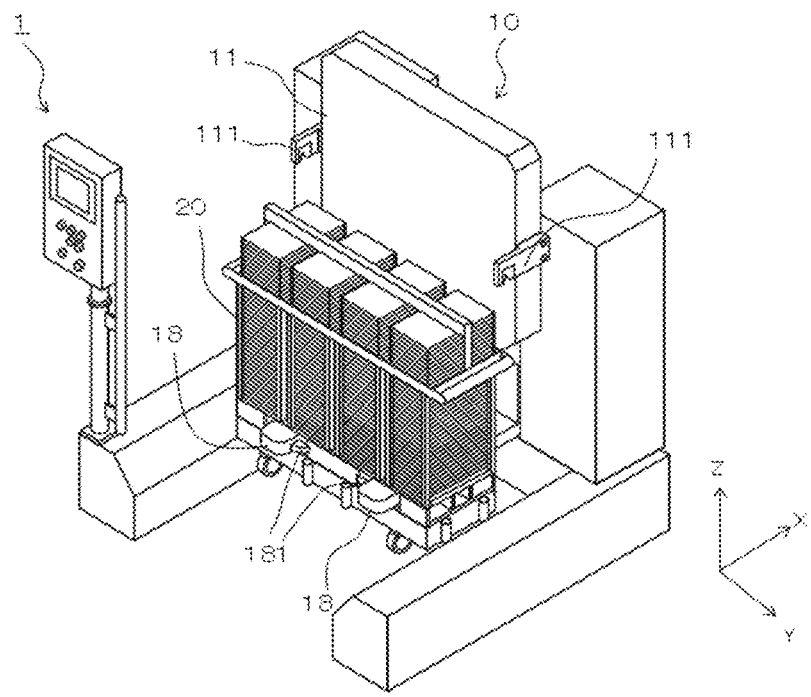
[Fig.8]
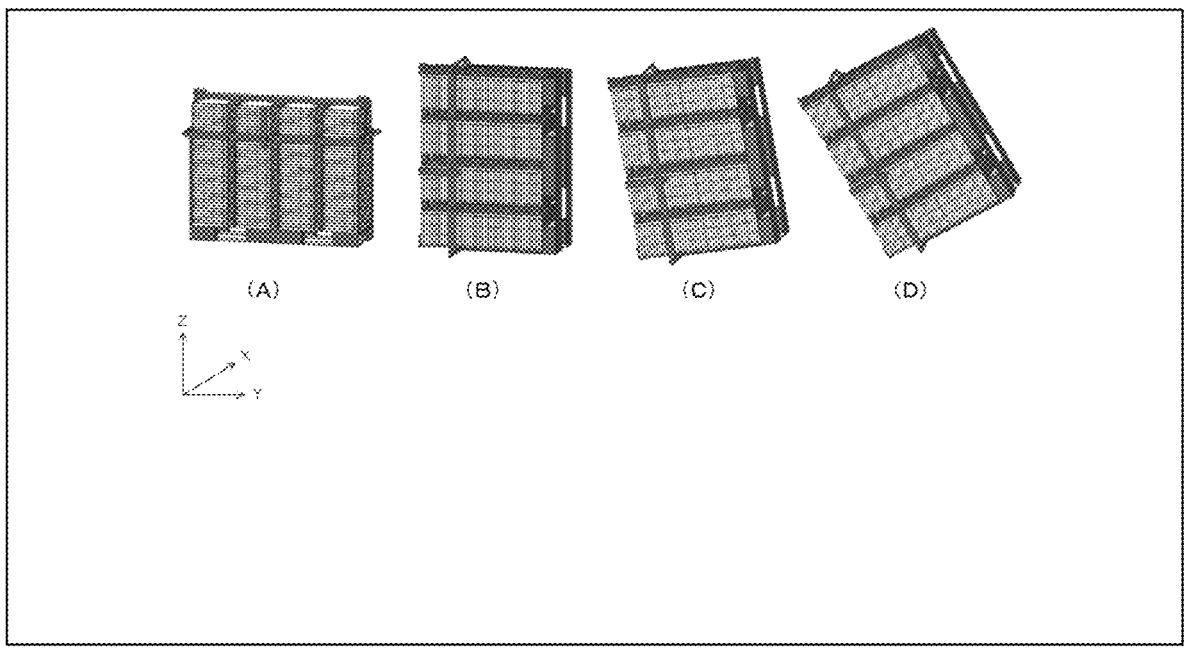
(A)     (B)     (C)     (D)

[Fig.9]
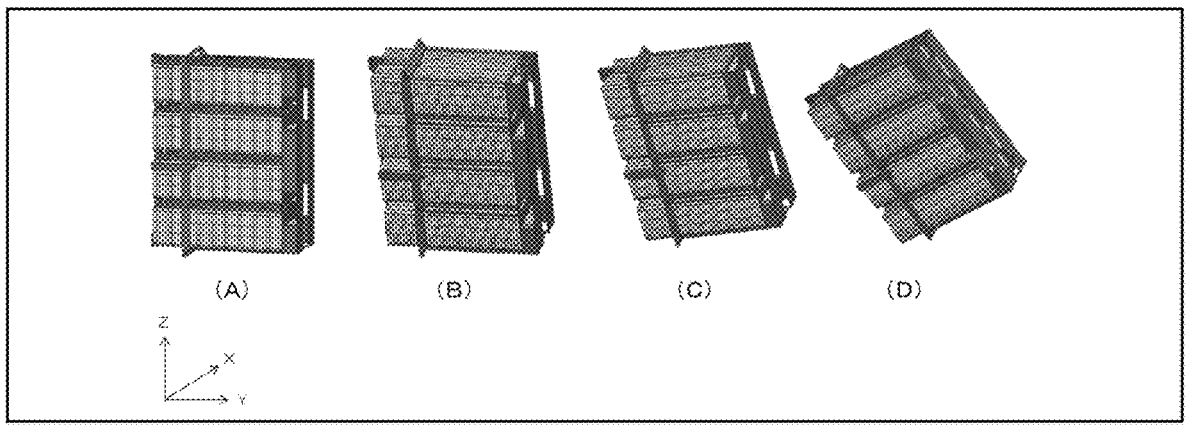
(A)  (B)  (C)  (D)
[Fig.10]
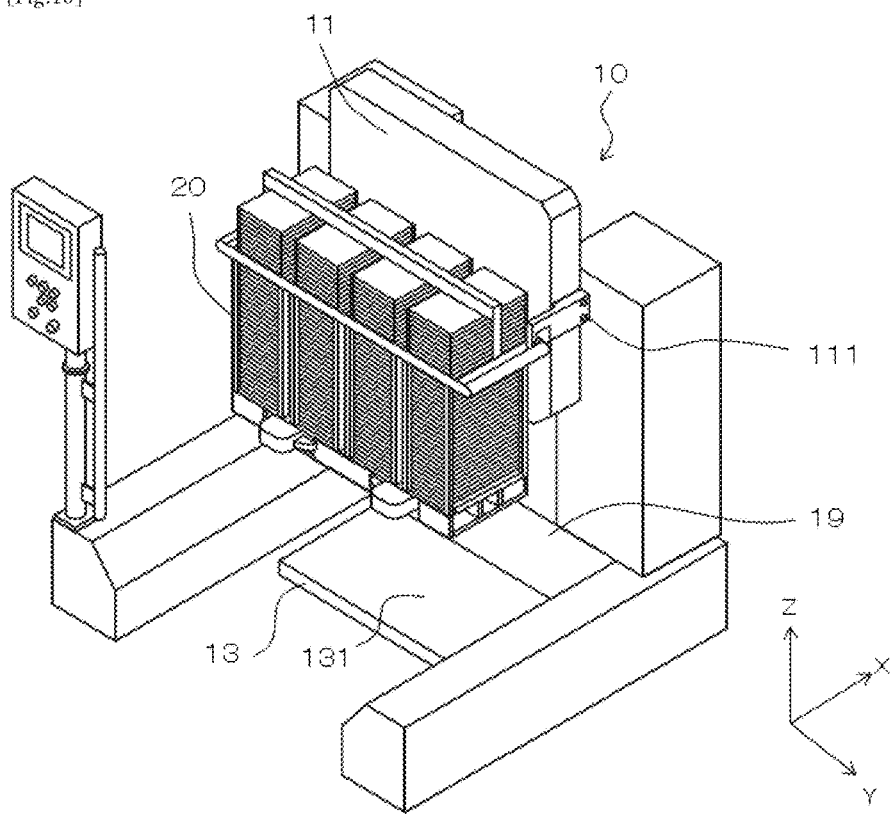

[Fig.11]
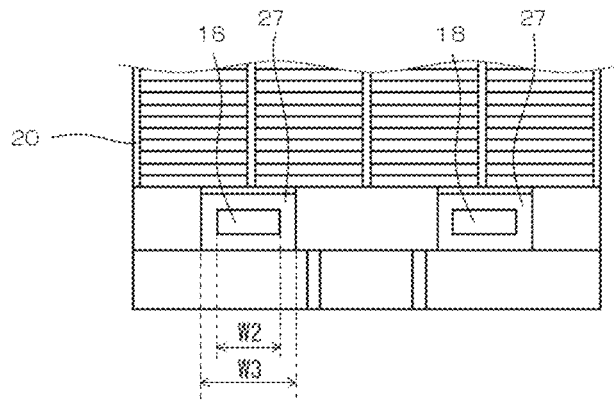
[Fig.12]
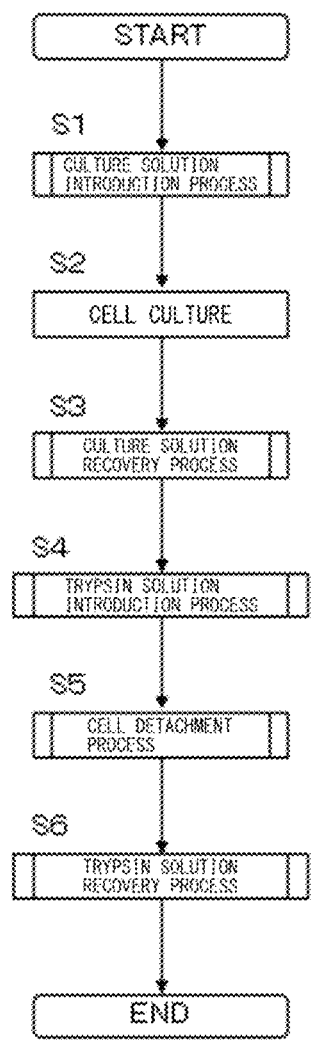

[Fig.13]
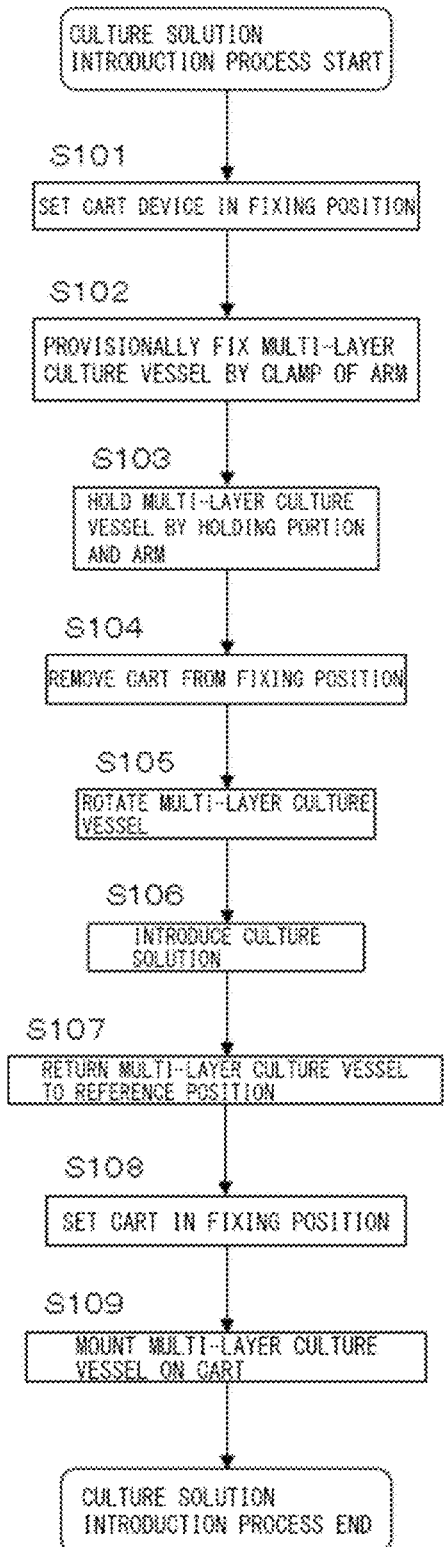

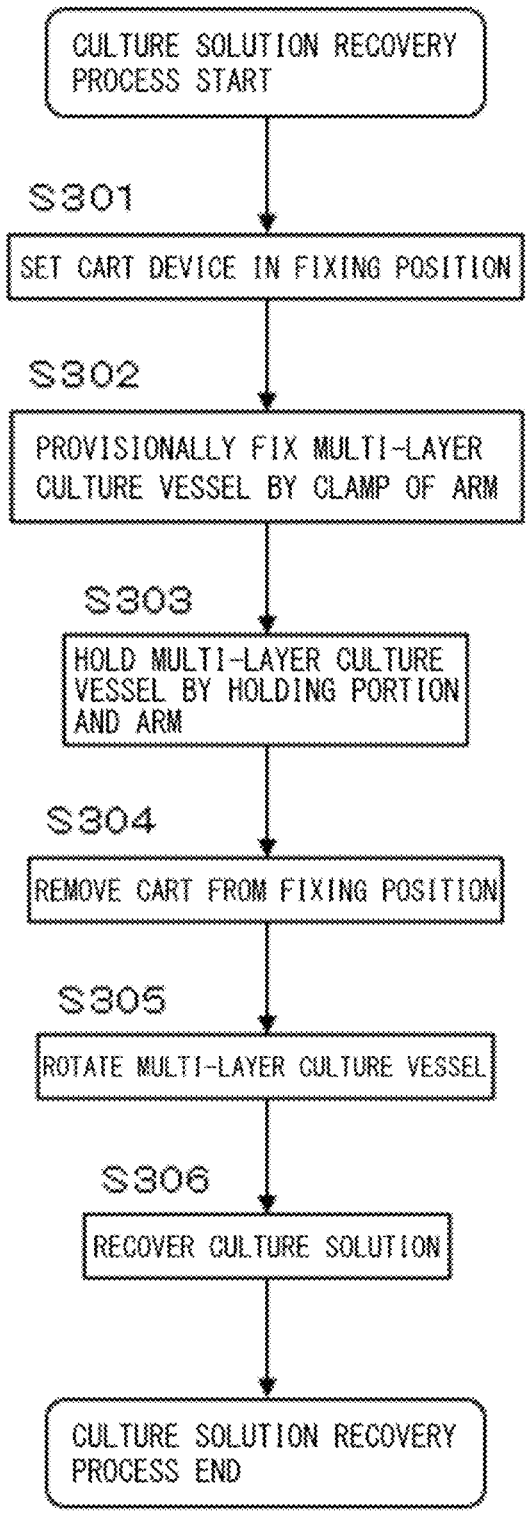
[Fig.14]

[Fig.15]
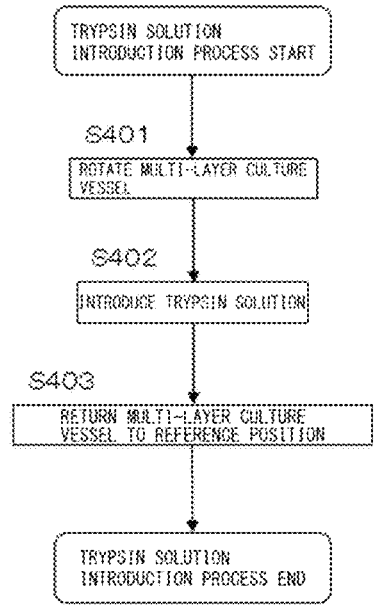
[Fig.16]
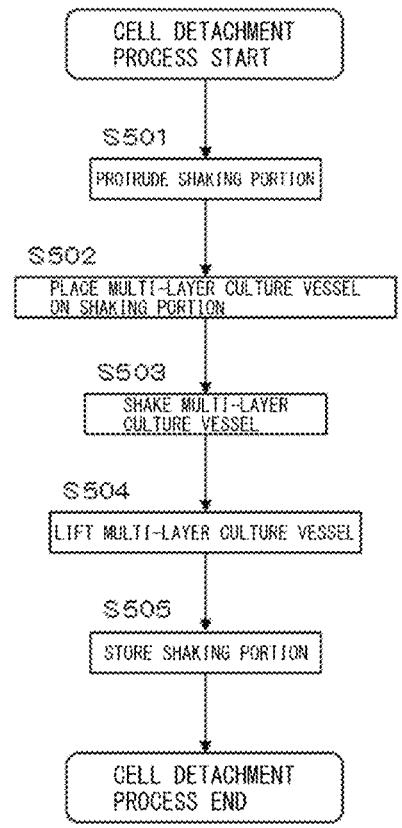

[Fig.17]
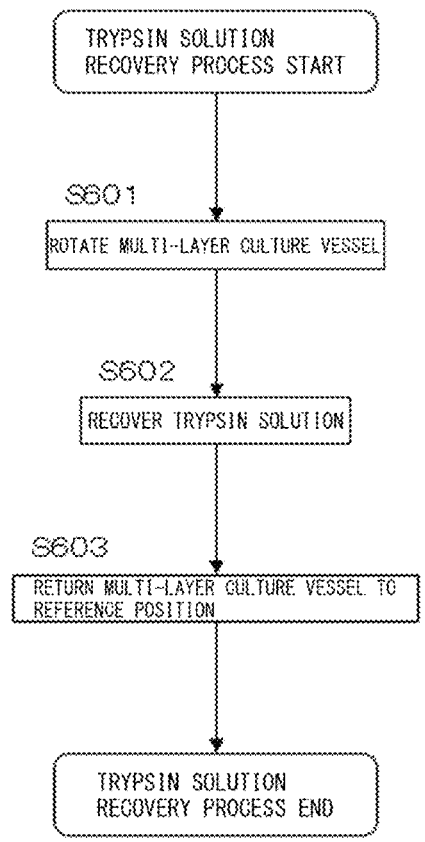
[Fig.18]
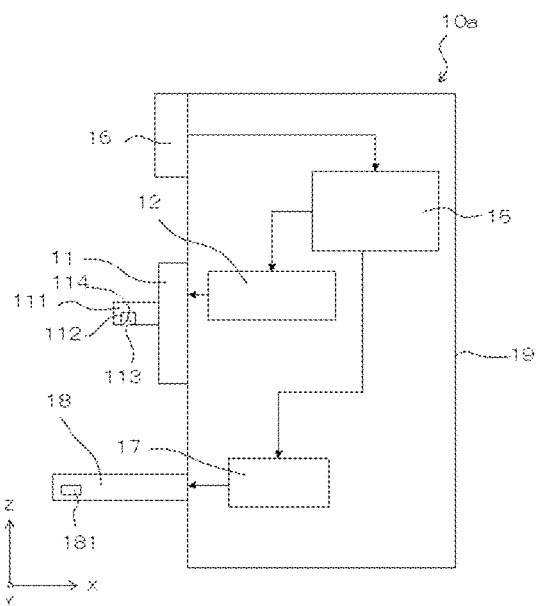

MULTI-LAYER CULTURE VESSEL OPERATION SYSTEM, MULTI-LAYER CULTURE VESSEL OPERATIONAL DEVICE, AND MULTI-LAYER CULTURE VESSEL OPERATION METHOD

TECHNICAL FIELD

The present invention relates to a multi-layer culture vessel operation system, a multi-layer culture vessel operational device, and a multi-layer culture vessel operation method for performing operation of handling a multi-layer culture vessel including a plurality of trays.

BACKGROUND ART

Cell culture techniques whereby cells seeded in a culture solution are cultured using a multi-layer culture vessel including a plurality of trays in order to culture cells in large quantity are known in recent years. In such cell culture techniques, to reduce the burden on an operator, a multi-layer culture vessel operational device for performing handling operation such as holding and rotating the multi-layer culture vessel is used to introduce or recover, for example, the culture solution seeded with the cells into or from the multi-layer culture vessel (see Patent Literature (PTL) 1).

CITATION LIST

Patent Literature

PTL 1: Japanese Patent Application Laid-Open No. 2015-505472

SUMMARY

Technical Problem

In typical cell culture, cultured cells adhere to the wall surface of a multi-layer culture vessel. Hence, the following process is performed: After recovering the culture solution from the multi-layer culture vessel, a trypsin solution is introduced into the multi-layer culture vessel, the multi-layer culture vessel is shaken to detach the cells from the wall surface, and the trypsin solution together with the detached cells is recovered. Conventionally, after introducing the trypsin solution into the multi-layer culture vessel, in order to perform the detachment process, the multi-layer culture vessel is manually removed from a multi-layer culture vessel operational device and placed on a dedicated shaking device to shake the multi-layer culture vessel. After this, in order to recover the trypsin solution, the multi-layer culture vessel is mounted on the multi-layer culture vessel operational device again. This increases the burden on the operator. Improvement in workability is therefore needed.

The present invention relates to a multi-layer culture vessel operation system, a multi-layer culture vessel operational device, and a multi-layer culture vessel operation method that can perform operation in cell culture and particularly a series of processes of trypsin solution introduction, cell detachment, and trypsin solution recovery in a state in which a multi-layer culture vessel remains mounted on the multi-layer culture vessel operational device.

Solution to Problem

A multi-layer culture vessel operation system according to the present invention is a multi-layer culture vessel operation system including: a cart device movable with a multi-layer culture vessel including a plurality of trays mounted thereon; and an operational device capable of holding and rotating the multi-layer culture vessel, wherein the cart device includes: a cart having wheels; and a fixing part that is removably mounted on the cart, and fixes the multi-layer culture vessel to the cart, wherein the operational device includes: a rotating portion that holds the multi-layer culture vessel together with the fixing part, and performs a rotation operation of rotating the multi-layer culture vessel around at least one of a first rotation axis and a second rotation axis; a shaking portion that holds the multi-layer culture vessel together with the fixing part, and performs a shaking operation of shaking the multi-layer culture vessel in a horizontal direction; and a control portion that controls operations of the rotating portion and the shaking portion, and wherein the control portion causes the shaking portion to perform the shaking operation following the rotation operation by the rotating portion, without returning the multi-layer culture vessel to the cart.

In the multi-layer culture vessel operation system, the control portion may cause the rotating portion to reciprocatingly swing the multi-layer culture vessel around the first rotation axis or the second rotation axis.

In the multi-layer culture vessel operation system, the shaking portion may be capable of being stored inside a body of the operational device, and the control portion may cause the shaking portion to protrude from the body of the operational device when the shaking operation is performed.

In the multi-layer culture vessel operation system, the control portion may cause the shaking portion to receive the multi-layer culture vessel together with the fixing part directly from the rotating portion, when the shaking operation is performed.

In the multi-layer culture vessel operation system, each of the rotating portion and the shaking portion may include an electric motor, and be driven by electric power.

A multi-layer culture vessel operational device according to a first aspect of the present invention is a multi-layer culture vessel operational device capable of receiving, from a cart movable with a multi-layer culture vessel including a plurality of trays mounted thereon, the multi-layer culture vessel and holding and rotating the multi-layer culture vessel, the multi-layer culture vessel operational device including: a rotating portion that holds the multi-layer culture vessel and performs a rotation operation of rotating the multi-layer culture vessel around at least one of a first rotation axis and a second rotation axis: a shaking portion that holds the multi-layer culture vessel and performs a shaking operation of shaking the culture vessel in a horizontal direction; and a control portion that controls operations of the rotating portion and the shaking portion, wherein the control portion causes the shaking portion to perform the shaking operation following the rotation operation by the rotating portion, without returning the multi-layer culture vessel to the cart.

In the multi-layer culture vessel operational device according to the first aspect, the control portion may cause the shaking portion to receive the multi-layer culture vessel together with the fixing part directly from the rotating portion, when the shaking operation is performed.

A multi-layer culture vessel operational device according to a second aspect of the present invention is a multi-layer culture vessel operational device including: a support member that supports a multi-layer culture vessel including a plurality of trays so as to be vertically movable: a locking part that fixes the multi-layer culture vessel in cooperation with the support member: a rotating portion that performs a rotation operation of rotating the support member around a first rotation axis and a second rotation axis; and a control portion that controls operations of the support member and the rotating portion, wherein the control portion has: a cell detachment function of performing a cell detachment process by causing the rotating portion to reciprocatingly swing the multi-layer culture vessel in a first direction and a second direction around the first rotation axis or the second rotation axis; and a stop mode of, while the cell detachment function is performed, stopping movement of the multi-layer culture vessel for a designated time when switching from the rotation operation in the first direction to the rotation operation in the second direction and when switching from the rotation operation in the second direction to the rotation operation in the first direction.

In the multi-layer culture vessel operational device according to the second aspect, each of the plurality of trays may have a first side surface, a second side surface adjacent to the first side surface, a third side surface adjacent to the second side surface, and a fourth side surface adjacent to the third side surface, and the control portion may have a side surface adhering cell recovery function of operating the rotating portion so that a trypsin solution will collide with the first side surface, the second side surface, the third side surface, and the fourth side surface in the stated order.

In the multi-layer culture vessel operational device, the rotating portion may include an electric motor, and be driven by electric power.

A multi-layer culture vessel operation method according to a first aspect of the present invention is a multi-layer culture vessel operation method of operating a multi-layer culture vessel including a plurality of trays using an operational device that includes: a rotating portion that holds the multi-layer culture vessel and performs a rotation operation of rotating the multi-layer culture vessel; and a shaking portion that holds the multi-layer culture vessel and performs a shaking operation of shaking the multi-layer culture vessel in a horizontal direction, the multi-layer culture vessel operation method including causing the shaking portion to perform the shaking operation following the rotation operation by the rotating portion.

A multi-layer culture vessel operation method according to a second aspect of the present invention is a multi-layer culture vessel operation method of operating a multi-layer culture vessel including a plurality of trays and in which a trypsin solution introduced, using an operational device that includes: a support member that supports the multi-layer culture vessel so as to be vertically movable: a locking part that fixes the multi-layer culture vessel in cooperation with the support member: a rotating portion that performs a rotation operation of rotating the support member around a first rotation axis and a second rotation axis; and a control portion that controls operations of the support member and the rotating portion, the multi-layer culture vessel operation method including stopping, while a cell detachment process is performed by causing the rotating portion to reciprocatingly swing the multi-layer culture vessel in a first direction and a second direction around the first rotation axis or the second rotation axis, movement of the multi-layer culture vessel for a designated time when switching from the rotation operation in the first direction to the rotation operation in the second direction and when switching from the rotation operation in the second direction to the rotation operation in the first direction.

In the multi-layer culture vessel operation method according to the second aspect, each of the plurality of trays may have a first side surface, a second side surface adjacent to the first side surface, a third side surface adjacent to the second side surface, and a fourth side surface adjacent to the third side surface, and, after the cell detachment process, the rotating portion may be operated so that the trypsin solution will collide with the first side surface, the second side surface, the third side surface, and the fourth side surface in the stated order.

Advantageous Effects of Invention

According to the present invention, a series of processes of trypsin solution introduction, cell detachment, and trypsin solution recovery can be performed in a state in which a multi-layer culture vessel remains mounted on a multi-layer culture vessel operational device, so that workability in cell culture can be improved.

BRIEF DESCRIPTION OF DRAWINGS

FIG. 1 is a diagram for explaining a multi-layer culture vessel according to Embodiment 1.

FIG. 2 is a diagram for explaining a method of distributing a liquid to each tray in the multi-layer culture vessel.

FIG. 3 is a perspective diagram illustrating a multi-layer culture vessel operation system according to Embodiment 1.

FIG. 4 is a perspective diagram for explaining a cart device according to Embodiment 1.

FIG. 5 is a block diagram for explaining a multi-layer culture vessel operational device according to Embodiment 1.

FIG. 6 is a diagram for explaining the relationship between a locked part of a fixing part and a locking part of the multi-layer culture vessel operational device.

FIG. 7 is a perspective diagram illustrating a state in which the multi-layer culture vessel is provisionally fixed to arms.

FIG. 8 is a diagram illustrating an example of a rotation operation of a rotating portion around a rotation axis X1.

FIG. 9 is a diagram illustrating an example of a rotation operation of the rotating portion around a rotation axis X2 and a rotation operation of the rotating portion around the rotation axes X1 and X2.

FIG. 10 is a perspective diagram illustrating a state in which a shaking portion is protruded in the multi-layer culture vessel operational device.

FIG. 11 is a diagram for explaining the relationship between the arms and insertion holes in a shaking operation.

FIG. 12 is a flowchart illustrating a cell culture process according to Embodiment 1.

FIG. 13 is a flowchart illustrating a culture solution introduction process in step S1.

FIG. 14 is a flowchart illustrating a culture solution recovery process in step S3.

FIG. 15 is a flowchart illustrating a trypsin solution introduction process in step S4.

FIG. 16 is a flowchart illustrating a cell detachment process in step S5.

FIG. 17 is a flowchart illustrating a trypsin solution recovery process in step S6.

FIG. 18 is a block diagram for explaining a multi-layer culture vessel operational device according to Embodiment 2.

DESCRIPTION OF EMBODIMENTS

Embodiment 1

A multi-layer culture vessel operation system 1 according to Embodiment 1 will be described below. The multi-layer culture vessel operation system 1 according to this embodiment is a system for operating (handling) a multi-layer culture vessel 30 used in cell culture and the like. The multi-layer culture vessel 30 according to this embodiment will be described first. FIG. 1 is a diagram for explaining the multi-layer culture vessel 30 according to this embodiment, and is a sectional diagram illustrating the multi-layer culture vessel 30. The multi-layer culture vessel 30 has a structure in which a plurality of trays 31 are stacked to culture cells in large quantity, as illustrated in FIG. 1. In the case of culturing cells in the multi-layer culture vessel 30, for example as illustrated in (A) in FIG. 2, the multi-layer culture vessel 30 is tilted about 90° so that a vent cap 32 will be on the lower side. The vent cap 32 and a pump are then connected, and a culture solution seeded with the cells is introduced into the multi-layer culture vessel 30 by the pump. After this, as illustrated in (B) in FIG. 2, the multi-layer culture vessel 30 is returned to the upright position, as a result of which the culture solution is distributed to each tray 31 in the multi-layer culture vessel 30. Thus, cell culture is performed in each tray 31.

After the cell culture, a culture solution recovery process of recovering the culture solution from the multi-layer culture vessel 30, a trypsin solution introduction process of introducing a trypsin solution into the multi-layer culture vessel 30 to detach cells adhering to the wall surface of the multi-layer culture vessel 30, and a trypsin solution recovery process of recovering the trypsin solution containing the detached cells from the multi-layer culture vessel 30 are performed. In these processes, too, an operation of introducing or recovering the culture solution or the trypsin solution by, for example, tilting the multi-layer culture vessel 30 is needed. However, in the case where an operator manually operates the multi-layer culture vessel 30, the burden on the operator increases as the multi-layer culture vessel 30 containing the culture solution or the trypsin solution is heavy. In addition, due to manual operation, the operation may vary, or the operator may unnecessarily touch the multi-layer culture vessel 30 and consequently damage the multi-layer culture vessel and cause contamination. There is thus a need for a system for operating the multi-layer culture vessel 30, such as the multi-layer culture vessel operation system 1 according to this embodiment.

FIG. 3 is a perspective diagram illustrating the multi-layer culture vessel operation system 1 according to this embodiment. As illustrated in FIG. 3, the multi-layer culture vessel operation system 1 according to this embodiment includes a multi-layer culture vessel operational device 10 and a cart device 20. Each of the components will be described below.

FIG. 4 is a perspective diagram for explaining the cart device 20 according to this embodiment. As illustrated in (A) in FIG. 4, the cart device 20 includes a cart 21 having wheels 22, and a fixing part 23 that fixes the multi-layer culture vessel 30 to the cart 21. In the cart device 20, the cart 21 and the fixing part 23 are removably attachable to each other. Specifically, by lifting the fixing part 23 upward (Z-axis positive direction) with respect to the cart 21, the fixing part 23 can be removed from the cart 21, as illustrated in (B) in FIG. 4. By placing the fixing part 23 on the cart 21, the fixing part 23 can be attached to the cart 21. The cart 21 and the fixing part 23 have respective fitting portions (not illustrated) that fit together. Thus, the cart 21 and the fixing part 23 are removably attachable to each other only in the vertical direction (Z-axis direction), and are fixed in the horizontal direction (XY-axis direction). This can prevent the fixing part 23 from falling from the cart 21 during movement of the cart device 20.

The fixing part 23 can simultaneously fix a plurality of multi-layer culture vessels 30 in a state in which the plurality of multi-layer culture vessels 30 are arranged side by side, as illustrated in FIG. 4. In this embodiment, the cart device 20 is configured to carry four multi-layer culture vessels 30 at the maximum. However, the present invention is not limited to this. The cart device 20 may be configured to carry one to three multi-layer culture vessels 30 at the maximum, or configured to carry five or more multi-layer culture vessels 30.

As illustrated in FIG. 4, the fixing part 23 includes a pedestal 24 on which the multi-layer culture vessel 30 is placed, a frame member 25 that guards the four long sides of the multi-layer culture vessel 30 to keep the multi-layer culture vessel 30 from being misaligned in the horizontal direction (XY-axis direction), and a fastening member 26 that is latched to the frame member 25 and, when the multi-layer culture vessel 30 is rotated, guards the multi-layer culture vessel 30 so as not to project upward (Z-axis direction). For example, the operator can fix the multi-layer culture vessel 30 to the fixing part 23, by placing the multi-layer culture vessel 30 on the pedestal 24 within the frame member 25 and then latching the fastening member 26 and the frame member 25 together by pressing the upper side of the multi-layer culture vessel 30 with the fastening member 26.

The fixing part 23 includes a locked part 28 that is locked by a locking part 111 in the multi-layer culture vessel operational device 10, as described later. In this embodiment, the locked part 28 is formed continuously in a part of the frame member 25 that extends along the side surface of the multi-layer culture vessel 30 in the arrangement direction of the multi-layer culture vessels 30. The locked part 28 is a thin plate-like member having a length W1, as illustrated in FIG. 4.

The multi-layer culture vessel operational device 10 according to this embodiment will be described below. FIG. 5 is a block diagram illustrating the multi-layer culture vessel operational device 10 according to this embodiment. As illustrated in FIG. 5, the multi-layer culture vessel operational device 10 includes a rotating portion 11, a rotation drive portion 12, a shaking portion 13, a shaking drive portion 14, a drive control portion 15, an operation portion 16, an arm drive portion 17, a pair of arms 18, and a body 19. The drive control portion 15 stores beforehand an operation program for operating the multi-layer culture vessel 30 in the culture solution introduction process of introducing the culture solution seeded with the cells into the multi-layer culture vessel 30, the culture solution recovery process of recovering the culture solution from the multi-layer culture vessel 30, the trypsin introduction process of introducing the trypsin solution into the multi-layer culture vessel 30, the cell detachment process of shaking the multi-layer culture vessel 30, the trypsin solution recovery process of recovering the trypsin solution from the multi-layer culture vessel 30, and the like. In this embodiment, based on the operation program, the drive control portion 15 controls the operation of the rotation drive portion 12 and the shaking drive portion 14 so as to cause the rotation drive portion 12 to rotate the rotating portion 11, and to cause the shaking drive portion 14 to shake the shaking portion 13 by controlling the operation of the shaking drive portion 14. In this embodiment, the rotation drive portion 12 and the shaking drive portion 14 each include an electric motor, and respectively drive the rotating portion 11 and the shaking portion 13 with supply of electric power.

As illustrated in FIGS. 3 and 5, the rotating portion 11 includes a pair of locking parts 111 that function as a member for holding the multi-layer culture vessel 30. The locking parts 111 are fixed on both sides of the rotating portion 11, and each have a recess 112 as illustrated in FIG. 5 and (A) to (C) in FIG. 6. The recess 112 has a tapered portion 113 and a groove portion 114. When the fixing part 23 is moved upward by the arm 18, the recess 112 can lock the locked part 28 of the fixing part 23 and clamp the fixing part 23 with the arm 18 to fix the fixing part 23 to the rotating portion 11, as illustrated in (B) in FIG. 6. This will be described later. (A) and (B) in FIG. 6 are diagrams for explaining the relationship between the locked part 28 and the locking part 111. (C) in FIG. 6 is an enlarged view of the locking part 111.

The multi-layer culture vessel operational device 10 includes the pair of arms 18 that function as a member for supporting the multi-layer culture vessel 30. The pair of arms 18 are insertable through two insertion holes 27 formed in the fixing part 23, as illustrated in FIG. 7. FIG. 7 is a perspective diagram illustrating a state in which the multi-layer culture vessel 30 is provisionally fixed to the arms 18. The pair of arms 18 are movable in the vertical direction (Z-axis direction) by the arm drive unit 17. The arm drive unit 17 drives the two arms 18 in the Z-axis direction to a height position at which the arms 18 can be inserted into the insertion holes 27 of the fixing part 23, based on an instruction by the drive control unit 15. Thus, the operator can move the cart device 20 toward the body 19 and insert the two arms 18 into the two insertion holes 27 of the fixing part 23. A clamp 181 is stored on the side of a tip part of each arm 18. When the arm 18 is inserted through the insertion hole 27, the clamp 181 protrudes from the side of the tip part of the arm 18 that has passed through the insertion hole 27. The drive control unit 15 then causes the arm drive unit 17 to drive the arms 18 upward (Z-axis positive direction) in a state in which the two arms 18 are inserted through the two insertion holes 27 of the fixing part 23, to lift the multi-layer culture vessel 30 to the position of the rotating portion 11. Consequently, the locking parts 111 of the rotating portion 11 and the locked part 28 of the fixing part 23 are locked together and the fixing part 23 is clamped by the rotating portion 11 with the pair of locking parts 111 and the pair of arms 18, so that the multi-layer culture vessel 30 together with the fixing part 23 is fixed to the rotating portion 11, as illustrated in (B) in FIG. 6. In this embodiment, the arm drive portion 17 can drive the pair of arms 18 by an electric motor or an air cylinder.

The drive control portion 15 then causes the rotation drive portion 12 to perform a rotation operation of rotating the rotating portion 11 around two axes, i.e. rotation axes X1 and X2, as indicated by reference signs R and P in FIG. 3. As illustrated in FIG. 3, the rotation axis X1 is a rotation axis extending in the X-axis direction. Thus, the rotating portion 11 and the multi-layer culture vessel 30 held by the rotating portion 11 can be rotated in a roll direction R. The rotation axis X2 is a rotation axis extending in the Y-axis direction. Thus, the rotating portion 11 and the multi-layer culture vessel 30 held by the rotating portion 11 can be rotated in a pitch direction P. In the rotation operation, the rotation in the roll direction R is possible within a range of less than ±180°. In this embodiment, the rotating portion 11 can be rotated in the roll direction R within a range of #120°. The rotation in the pitch direction P is possible within a range of less than +180°, too. In this embodiment, the rotating portion 11 can be rotated in the pitch direction P within a range of ±30°. In this embodiment, the rotation drive portion 12 includes an electric motor and/or an air cylinder for rotating the rotating portion 11 around the rotation axis X1 and an electric motor and/or an air cylinder for rotating the rotating portion 11 around the rotation axis X2, and thus can rotate the rotating portion 11 around the two axes.

FIG. 8 is a diagram illustrating an example of a rotation operation of the rotating portion 11 (multi-layer culture vessel 30) around the rotation axis X1. (A) in FIG. 8 illustrates a state in which the rotating portion 11 has lifted the multi-layer culture vessel 30 (reference position). In this embodiment, for example, the rotation drive portion 12 can rotate the rotating portion 11 (multi-layer culture vessel 30) 90° to the left around the rotation axis X1 from the reference position illustrated in (A) in FIG. 8, as illustrated in (B) in FIG. 8. Moreover, the rotation drive portion 12 can rotate the rotating portion 11 (multi-layer culture vessel 30) 100° to the left around the rotation axis X1 from the reference position as illustrated in (C) in FIG. 8, and can rotate the rotating portion 11 (multi-layer culture vessel 30) 120° to the left around the rotation axis X1 from the reference position as illustrated in (D) in FIG. 8. Further, the rotation drive portion 12 can rotate the rotating portion 11 (multi-layer culture vessel 30) within a range of 0°) to 120° to the right from the reference position. In this way, the rotation drive portion 12 can rotate the rotating portion 11 (multi-layer culture vessel 30) in the roll direction R within a range of ±0° to ±120° around the rotation axis X1 from the reference position.

FIG. 9 is a diagram illustrating an example of a rotation operation of the rotating portion 11 (multi-layer culture vessel 30) around the rotation axis X2 and a rotation operation of the rotating portion 11 (multi-layer culture vessel 30) around the two axes, i.e. the rotation axes X1 and X2. The rotation drive portion 12 can rotate the rotating portion 11 (multi-layer culture vessel 30) in the pitch direction P around the rotation axis X2 from the reference position illustrated in (A) in FIG. 9. For example, in the example illustrated in (B) in FIG. 9, the rotating portion 11 (multi-layer culture vessel 30) is rotated 20° around the rotation axis X2 so as to tilt an upper part of the rotating portion 11 (multi-layer culture vessel 30) forward (X-axis negative direction). The rotation drive portion 12 can also rotate the rotating portion 11 (multi-layer culture vessel 30) around the rotation axis X2 so as to tilt a lower part of the rotating portion 11 (multi-layer culture vessel 30) forward (X-axis negative direction). In this way, the rotation drive portion 12 can rotate the rotating portion 11 (multi-layer culture vessel 30) in the pitch direction P within a range of ±0° to ±30° around the rotation axis X2 from the reference position.

The rotation drive portion 12 can rotate the rotating portion 11 (multi-layer culture vessel 30) in the roll direction R around the rotation axis X1 and in the pitch direction P around the rotation axis X2, as illustrated in (C) and (D) in FIG. 9. For example, in the example illustrated in (C) in FIG. 9, the rotating portion 11 (multi-layer culture vessel 30) is rotated 100° to the left around the rotation axis X1, and also rotated 20° around the rotation axis X2 so as to tilt the upper part of the rotating portion 11 (multi-layer culture vessel 30) forward (X-axis negative direction). In the example illustrated in (D) in FIG. 9, the rotating portion 11 (multi-layer culture vessel 30) is rotated 120° to the left around the rotation axis X1, and also rotated 20° around the rotation axis X2 so as to tilt the upper part of the rotating portion 11 (multi-layer culture vessel 30) forward (X-axis negative direction).

The rotation drive portion 12 can also perform a swinging operation of reciprocatingly rotating the rotating portion 11

(multi-layer culture vessel 30) around the rotation axis X1 or the rotation axis X2. For example, the rotation drive portion 12 can perform a swinging operation around the rotation axis X1, by reciprocatingly rotating the rotating portion 11 (multi-layer culture vessel 30) in the roll direction R within a range of ±120° around the rotation axis X1. The rotation drive portion 12 can also perform a swinging operation around the rotation axis X2, by reciprocatingly rotating the rotating portion 11 (multi-layer culture vessel 30) in the pitch direction P within a range of ±20° around the rotation axis X2 so as to tilt the upper part of the rotating portion 11 (multi-layer culture vessel 30) forward (X-axis negative direction) and then tilt the lower part of the rotating portion 11 (multi-layer culture vessel 30) forward (X-axis negative direction).

The shaking portion 13 is stored inside the body 19 of the multi-layer culture vessel operational device 10 when not performing the below-described shaking operation. When performing the shaking operation, the shaking portion 13 is protruded to the outside of the body 19 by the shaking drive portion 14 under control of the drive control portion 15, as illustrated in FIG. 10. FIG. 10 is a perspective diagram illustrating a state in which the shaking portion 13 is protruded in the multi-layer culture vessel operational device 10. The shaking portion 13 has an upper surface 131 wide enough to have the multi-layer culture vessel 30 together with the fixing part 23 placed thereon, and can perform a shaking operation in the horizontal direction with the multi-layer culture vessel 30 together with the fixing part 23 being placed on the upper surface 131. The shaking portion 13 also has a fitting portion (not illustrated) into which the fixing part 23 is to be fitted, as in the cart 21. Thus, the shaking portion 13 is removably attachable to the fixing part 23 in the vertical direction (Z-axis direction), while restricting the movement of the fixing part 23 in the horizontal direction (XY-axis direction) to prevent the fixing part 23 from falling from the shaking portion 13. The shaking drive portion 14 can cause the shaking portion 13 to perform any shaking operation as long as it is in the horizontal direction (XY-axis direction). For example, the shaking drive portion 14 may cause the shaking portion 13 to perform various shaking operations, such as a shaking operation from side to side (reciprocation operation in the Y-axis direction), a shaking operation back and forth (reciprocation operation in the X-axis direction), and a shaking operation in a figure-of-eight direction (operation in a combination of the X-axis direction and the Y-axis direction).

In this embodiment, the drive control portion 15 can cause the shaking portion 13 to perform the shaking operation following the rotation operation by the rotating portion 11. In this case, after the rotation operation by the rotating portion 11 ends, the drive control portion 15 controls the arm drive portion 17 to drive the pair of arms 18 downward (Z-axis negative direction) so that the multi-layer culture vessel 30 together with the fixing part 23 will be placed on the upper surface 131 of the shaking portion 13. The drive control portion 15 then controls the shaking drive portion 14 to cause the shaking portion 13 to perform the shaking operation of shaking the multi-layer culture vessel 30. In this embodiment, the shaking operation is performed in a state in which the arms 18 remain protruding without being stored in the body 19. In this embodiment, the inner width W3 of the insertion hole 27 is greater than the sum of the outer width W2 of the arm 18 and the shaking width of the shaking portion 13 as illustrated in FIG. 11, so that the shaking operation can be performed in a state in which the arm 18 is inserted through the insertion hole 27. In the shaking operation, the clamp 181 is stored inside the arm 18. FIG. 11 is a diagram for explaining the relationship between the arms 18 and the insertion holes 27 in the shaking operation.

The drive control portion 15 can cause the rotating portion 11 to perform the rotation operation following the shaking operation by the shaking portion 13. In this case, after the shaking operation by the shaking portion 13 ends, the drive control portion 15 controls the arm drive portion 17 to drive the pair of arms 18 upward (Z-axis positive direction) so that the multi-layer culture vessel 30 together with the fixing part 23 will be lifted upward. The drive control portion 15 then controls the shaking drive portion 14 to store the shaking portion 13 inside the body 19, and subsequently controls the rotation drive portion 12 to cause the rotating portion 11 to perform the rotation operation.

The operation portion 16 is a device for the operator to input instructions, and may include, for example, a touch panel. By operating the operation portion 16, the operator can transmit, to the drive control portion 15, an instruction such as starting, halting, or ending the operation program stored in the drive control portion 15 beforehand, to start, halt, or end the operation of the rotating portion 11 or the shaking portion 13, for example. Moreover, by operating the operation portion 16, the operator can cause the drive control portion 15 to store a new program or partially change the stored operation program. For example, by operating the operation portion 16, the operator can change the inclination angle of the rotation axis X1 of the rotating portion 11 from 100° to 120° in the culture solution recovery process of recovering the culture solution from the multi-layer culture vessel 30.

The cell culture process in the multi-layer culture vessel operation system 1 according to this embodiment will be described below. FIG. 12 is a flowchart illustrating the cell culture process in the multi-layer culture vessel operation system 1 according to this embodiment. Each process performed by the multi-layer culture vessel operational device 10 is started when the operator presses a process start button in the operation portion 16. When the process ends, the operation of the multi-layer culture vessel operational device 10 ends. Accordingly, in the case of operating the multi-layer culture vessel operational device 10, the operator presses the process start button in the operation portion 16 for each process to proceed with each process. The operation program of the operation of the multi-layer culture vessel operational device 10 in each process is stored in the drive control portion 15 beforehand, and the operator simply presses the same process start button to cause the drive control portion 15 to instruct the rotation drive portion 12 or the shaking drive portion 14 to perform the operation corresponding to each process by operating the rotating portion 11 or the shaking portion 13.

In step S1, the culture solution introduction process of introducing the culture solution seeded with the cells into the multi-layer culture vessel 30 is performed. FIG. 13 is a flow chart illustrating the culture solution introduction process in step S1. First, in step S101, the operator sets the cart device 20 carrying the empty multi-layer culture vessel 30 to a fixing position of the multi-layer culture vessel operational device 10. The fixing position is a position at which the pair of arms 18 are at the same height as the insertion holes 27 of the cart device 20 and, in the case where the cart device 20 is set in the fixing position, the two arms 18 are inserted through the two insertion holes 27 of the fixing part 23 and the tip part of each arm 18 protrudes from the corresponding insertion hole 27. The operator then operates the operation portion 16 to perform a process in step S102.

In step S102, the rotation drive portion 12 causes the clamp 181 to protrude from the tip part of each arm 18, and the multi-layer culture vessel 30 fixed by the fixing part 23 is, together with the fixing part 23, provisionally fixed to the arms 18. Further, in step S103, the arm drive portion 17 drives the pair of arms 18 fixing the multi-layer culture vessel 30, upward (Z-axis positive direction). Thus, the fixing part 23 is removed from the cart 21 of the cart device 20, and the multi-layer culture vessel 30 together with the fixing part 23 is lifted upward (Z-axis positive direction) by the arms 18 until it comes into contact with the locking parts 111 of the rotating portion 11. Consequently, the fixing part 23 is clamped by the locking parts 111 and the arms 18, and the multi-layer culture vessel 30 together with the fixing part 23 is held by the rotating portion 11.

In step S104, the operator removes the cart 21 from the fixing position. The operator then operates the operation portion 16 to perform a process in step S105. In step S105, the rotation drive portion 12 performs a process of rotating the rotating portion 11. For example, the drive control portion 15 can rotate the multi-layer culture vessel 30 90° to the left as illustrated in (B) in FIG. 8, by controlling the rotating portion 11 to rotate 90° to the left around the rotation axis X1 from the reference position.

In step S106, the operator introduces the culture solution seeded with the cells into the multi-layer culture vessel 30. For example, the operator may open the vent cap 32 of the multi-layer culture vessel 30, connect the pump (not illustrated) to the vent cap 32, and introduce the culture solution into the multi-layer culture vessel 30 using the pump. Thus, the culture solution accumulates on the lower side in the multi-layer culture vessel 30 rotated 90°, as illustrated in (A) in FIG. 2. In the case where the introduction of the culture solution is completed, the operator closes the vent cap 32. The operator then operates the operation portion 16 to perform a process in step S107.

In step S107, the rotation drive portion 12 returns the multi-layer culture vessel 30 to the reference position, as illustrated in (A) in FIG. 9. Consequently, the culture solution is distributed to each tray 31 in the multi-layer culture vessel 30, as illustrated in (B) in FIG. 2. In step S108 which follows, the operator sets the cart 21 in the fixing position. The operator then operates the operation portion 16 to perform a process in step S109. In step S109, the arm drive portion 17 drives the pair of arms 18 downward (Z-axis negative direction), and the fixing part 23 fixing the multi-layer culture vessel 30 is mounted on the cart 21. This enables the operator to move the multi-layer culture vessel 30 in which the culture solution has been distributed, to a culture chamber or an incubator by the cart device 20.

Referring back to FIG. 12, in step S2, cell culture is performed for a predetermined time in the culture chamber or the incubator. In step S3, the culture solution recovery process of recovering the culture solution after the cell culture from the multi-layer culture vessel 30 is performed. FIG. 14 is a flowchart illustrating the culture solution recovery process in step S3.

As illustrated in FIG. 14, in steps S301 to S305, the cart device 20 is set in the fixing position (step S301), the multi-layer culture vessel 30 together with the fixing part 23 is provisionally fixed to the arms 18 (step S302), the multi-layer culture vessel 30 is lifted upward and clamped by the locking parts 111 and the arms 18 to be held by the rotating portion 11 (step S303), the operator removes the cart 21 from the fixing position (step S304), and the rotation operation of the multi-layer culture vessel 30 is performed (step S305), as in steps S101 to S105.

In step S305, the multi-layer culture vessel 30 may be rotated in the roll direction R around the rotation axis X1 and also rotated in the pitch direction P around the rotation axis X2, as illustrated in (C) and (D) in FIG. 9. In step S305, a draining process may be performed before the rotation operation. The draining process is a process of rotating the rotating portion 11 to remove droplets adhering to, for example, the side surface of each tray 31 in the multi-layer culture vessel 30. Specifically, in a state in which the multi-layer culture vessel 30 is rotated 90° in the roll direction R as illustrated in (B) in FIG. 8, the drive control portion 15 rotates the multi-layer culture vessel 30 +30° in the pitch direction P (i.e. tilts the upper part forward 30° in the pitch direction P), and subsequently rotates the multi-layer culture vessel 30 −30° in the pitch direction P (i.e. tilts the upper part backward 30° in the pitch direction P). It is thus possible to remove droplets scattered to the side surface of each tray 31 in the multi-layer culture vessel 30 by the culture solution.

In step S306, the operator recovers the culture solution from the multi-layer culture vessel 30. For example, the operator can recover the culture solution from the multi-layer culture vessel 30 by connecting the pump to the vent cap 32 of the multi-layer culture vessel 30, opening the vent cap 32, and sucking the culture solution with the pump.

Referring back to FIG. 12, in step S4, the trypsin solution introduction process of introducing the trypsin solution into the multi-layer culture vessel 30 in order to detach culture cells adhering to the wall surface of each tray 31 in the multi-layer culture vessel 30 is performed. FIG. 15 is a flowchart illustrating the trypsin solution introduction process in step S4.

First, in step S401, the multi-layer culture vessel 30 is rotated, as in step S105. For example, the multi-layer culture vessel 30 may be rotated 90° as illustrated in (B) in FIG. 9. In step S402, the operator introduces the trypsin solution into the multi-layer culture vessel 30. For example, the operator may open the vent cap 32 of the multi-layer culture vessel 30, connect the pump to the vent cap 32, and introduce the trypsin solution into the multi-layer culture vessel 30 using the pump, as in step S106. Thus, the trypsin solution accumulates on the lower side in the multi-layer culture vessel 30 rotated 90°, as illustrated in (A) in FIG. 2. In the case where the introduction of the trypsin solution is completed, the operator closes the vent cap 32. In step S403, the rotation drive portion 12 returns the multi-layer culture vessel 30 to the reference position as illustrated in (A) in FIG. 9, as in step S107. Consequently, the trypsin solution is distributed to each tray 31 in the multi-layer culture vessel 30, as illustrated in (B) in FIG. 2.

Referring back to FIG. 12, in step S5, the cell detachment process of detaching culture cells adhering to the wall surface of each tray 31 in the multi-layer culture vessel 30 is performed. FIG. 16 is a flowchart illustrating the cell detachment process in step S5. In this embodiment, the operator operates the operation portion 16 to perform a process in step S501.

In step S501, the shaking portion 13 stored inside the multi-layer culture vessel operational device 10 is protruded to the outside of the body 19. In step S502, the arm drive portion 17 drives the pair of arms 18 downward (Z-axis negative direction), as a result of which the multi-layer culture vessel 30 held by the rotating portion 11 is, together with the fixing part 23, placed on the upper surface 131 of the shaking portion 13.

In step S503, the shaking drive portion 14 performs the shaking operation of the shaking portion 13. The shaking drive portion 14 causes the shaking portion 13 to shake from side to side (Y-axis direction), back and forth (X-axis direction), or in a figure-of-eight direction (XY-axis direction), thus shaking the multi-layer culture vessel 30. As a result, the culture cells adhering to the wall surface of each tray 31 are detached. In step S504, the multi-layer culture vessel 30 is lifted upward by the pair of arms 18 and held by the rotating portion 11, as in step S103. In step S505, the shaking drive portion 14 stores the shaking portion 13 inside the multi-layer culture vessel operational device 10.

Referring back to FIG. 12, in step S6, the trypsin solution recovery process of recovering the trypsin solution containing the detached culture cells is performed. FIG. 17 is a flowchart illustrating the trypsin solution recovery process in step S6.

Specifically, in step S601, the rotation operation of the multi-layer culture vessel 30 is performed, as in step S305. For example, the multi-layer culture vessel 30 may be rotated in the roll direction R around the rotation axis X1 and also rotated in the pitch direction P around the rotation axis X2, as illustrated in (C) and (D) in FIG. 9. In step S601, the draining process may be performed before the rotation operation, as in step S305. In step S602, the operator recovers the trypsin solution from the multi-layer culture vessel 30 using the pump or the like, as in step S306. In step S603, the rotation drive portion 12 returns the multi-layer culture vessel 30 to the reference position.

As described above, the multi-layer culture vessel operational device 10 according to this embodiment integrally includes the rotating portion 11 that performs the rotation operation of the multi-layer culture vessel 30 and the shaking portion 13 that performs the shaking operation of the multi-layer culture vessel 30, and can cause the shaking portion 13 to perform the shaking operation following the rotation operation by the rotating portion 11 without returning the multi-layer culture vessel 30 to the cart 21. With such multi-layer culture vessel operational device 10 according to this embodiment, the series of processes, i.e. the culture solution recovery process, the trypsin solution introduction process, the cell detachment process, and the process of recovering the trypsin solution containing the detached culture cells, can be performed in a state in which the multi-layer culture vessel 30 remains held by the multi-layer culture vessel operational device 10, without the operator touching the multi-layer culture vessel 30.

With conventional techniques, after introducing the trypsin solution into the multi-layer culture vessel 30, the operator manually removes the multi-layer culture vessel 30 from the multi-layer culture vessel operational device, places the multi-layer culture vessel 30 on a dedicated shaker, shakes the multi-layer culture vessel 30 by the dedicated shaker, and then manually places the multi-layer culture vessel 30 on the multi-layer culture vessel operational device again to perform the trypsin solution recovery process. This increases the labor of the operator in the cell culture process. In addition, due to the manual operation by the operator, the operation may vary, or the operator may unnecessarily touch the multi-layer culture vessel 30 and consequently damage the multi-layer culture vessel 30 and contaminate the culture medium. According to this embodiment, such problems can be solved because the foregoing series of processes can be performed without the operator touching the multi-layer culture vessel 30.

In this embodiment, the rotation drive portion 12 and the shaking drive portion 14 each include an electric motor, and operate with supply of electric power. Multi-layer culture vessel operational devices including a rotation drive portion are conventionally known. In such a multi-layer culture vessel operational device, a hydraulic drive is used. However, since the hydraulic drive has the possibility of contaminating a clean room, the multi-layer culture vessel operational device is not usable in some clean rooms. In the multi-layer culture vessel operational device 10 according to this embodiment, on the other hand, an electric motor is used in each of the rotation drive portion 12 and the shaking drive portion 14. The multi-layer culture vessel operational device 10 is therefore usable regardless of clean rooms.

Embodiment 2

A multi-layer culture vessel operational device 10a according to Embodiment 2 mainly differs from the multi-layer culture vessel operational device 10 according to Embodiment 1 in that it does not include the shaking portion 13 and the shaking drive portion 14. Hereafter, the same components as in Embodiment 1 are given the same reference signs, and their description is omitted.

FIG. 18 is a block diagram illustrating the multi-layer culture vessel operational device 10a according to this embodiment. As illustrated in FIG. 18, the multi-layer culture vessel operational device 10a includes the rotating portion 11, the rotation drive portion 12, the drive control portion 15, the operation portion 16, the arm drive portion 17, the pair of arms 18, and the body 19. The drive control portion 15 stores beforehand an operation program for operating the multi-layer culture vessel 30 in the culture solution introduction process of introducing the culture solution seeded with the cells into the multi-layer culture vessel 30, the culture solution recovery process of recovering the culture solution from the multi-layer culture vessel 30, the trypsin introduction process of introducing the trypsin solution into the multi-layer culture vessel 30, the cell detachment process of shaking the multi-layer culture vessel 30, the trypsin solution recovery process of recovering the trypsin solution from the multi-layer culture vessel 30, and the like.

The rotation drive portion 12 includes a first electric motor that rotates the rotating portion 11 around the rotation axis X1 and a second electric motor that rotates the rotating portion 11 around the rotation axis X2.

The operation program causes the cell detachment process to be performed by the rotating portion 11 reciprocatingly swinging the multi-layer culture vessel 30 in a first direction (e.g. to the right direction) and in a second direction (e.g. to the left direction) around a first rotation axis or a second rotation axis. The operation program defines a stop mode in which the movement of the multi-layer culture vessel 30 is stopped for a designated time at the time of switching from the rotation operation in the first direction to the rotation operation in the second direction and at the time of switching from the rotation operation in the second direction to the rotation operation in the first direction.

With the stop mode, even in the case where the speed of the swinging operation is higher than the speed of the movement of the liquid in the vessel, by stopping the swinging operation for the designated time at the time of switching the direction of the rotation operation, the liquid in the vessel can reliably collide with the side surface (side wall) of the vessel. While it is important to swing the vessel at high speed for an effective cell detachment process, the delay (time lag) of the movement of the liquid which occurs at the time of swinging the vessel at high speed can be resolved in this way.

The operation program causes an operation of recovering cells adhering to the side surface of each tray 31 to be performed before the trypsin solution recovery process. In the case where each tray 31 is a rectangular tray having first to fourth side surfaces, the rotating portion 11 is operated so that the trypsin solution will collide with the first side surface, the second side surface, the third side surface, and the fourth side surface in this order. With such operation, the trypsin solution recovery process can be performed after recovering, in the trypsin solution, the cells adhering to the side surface of each tray 31.

The multi-layer culture vessel operational device 10a according to Embodiment 2 described above has the same advantageous effects as in Embodiment 1.

Moreover, according to Embodiment 2, the cell detachment process is possible without the shaking portion 13. Since the device structure is simple, the manufacturing costs can be reduced.

Furthermore, the stop mode can resolve the delay (time lag) of the movement of the liquid which occurs when swinging the vessel at high speed.

While some preferred embodiments of the present invention have been described above, the technical scope of the present invention is not limited to the foregoing embodiments. Various modifications and improvements can be made to the foregoing embodiments, and such modifications and improvements are also included in the technical scope of the present invention.

Although the foregoing embodiments describe an example in which the multi-layer culture vessel operation system 1 and the multi-layer culture vessel operational devices 10 and 10a are used in cell culture, the present invention is not limited to such. The multi-layer culture vessel operation system 1 and the multi-layer culture vessel operational devices 10 and 10a may be used in microorganism culture.

The multi-layer culture vessel operational devices 10 and 10a may each have any of the following structures, in addition to the foregoing embodiments.

In the case where the rotation drive portion 12 and the arm drive portion 17 are formed by an air cylinder, the multi-layer culture vessel operational devices 10 and 10a may each include a pressure sensor for monitoring the pressure of the air cylinder. By monitoring the air pressure of the air cylinder by the pressure sensor, a failure of the air cylinder can be detected.

The multi-layer culture vessel operational devices 10 and 10a may each include an area sensor. By constantly monitoring, by the area sensor, whether anyone comes near the multi-layer culture vessel operational device and in particular the rotating portion 11, safety can be improved.

The drive control portion 15 may be configured to count the number of times the rotating portion 11, the shaking portion 13, or the arms 18 are operated. The drive control portion 15 may then configured to predict when to replace an electric motor or an air cylinder included in the rotation drive portion 12, the shaking drive portion 14, or the arm drive portion 17, based on the number of times the rotating portion 11, the shaking portion 13, or the arms 18 are operated.

The drive control portion 15 may be configured to measure the total operation time of the rotating portion 11, the shaking portion 13, or the arms 18. The drive control portion 15 may then configured to predict when to replace an AC/DC power source, a battery, a fan, or the like, based on the total operation time of the rotating portion 11, the shaking portion 13, or the arms 18.

REFERENCE SIGNS LIST 1 multi-layer culture vessel operation system
10, 10a multi-layer culture vessel operational device
11 rotating portion
111 locking part
112 recess
113 tapered portion
114 groove portion
12 rotation drive portion
17 arm drive portion
13 shaking portion
131 upper surface
14 shaking drive portion
15 drive control portion
16 operation portion
18 arm
181 clamp
19 body
20 cart device
21 cart
22 wheels
23 fixing part
24 pedestal
25 frame member
26 fastening member
27 insertion hole
28 locked part
30) multi-laver culture vessel
31 tray
32 vent cap

The invention claimed is:

1. A multi-layer culture vessel operational device comprising:
a support member that supports a multi-layer culture vessel including a plurality of trays so as to be vertically movable;
a locking part that fixes the multi-layer culture vessel in cooperation with the support member;
a rotating portion that performs a rotation operation of rotating the support member around a first rotation axis and a second rotation axis; and
a control portion that controls operations of the support member and the rotating portion,
wherein the control portion has:
a cell detachment function of performing a cell detachment process by causing the rotating portion to reciprocatingly swing the multi-layer culture vessel in a first direction and a second direction around the first rotation axis or the second rotation axis at a speed higher than a speed of a movement of a liquid contained in the multi-layer culture vessel to generate time lag in the movement of the liquid contained in the multi-layer culture vessel, wherein the first direction and the second direction are opposite to each other; and
a stop mode of, while the cell detachment function is performed, stopping movement of the multi-layer culture vessel for a designated time when switching from the rotation operation in the first direction to the rotation operation in the second direction and when switching from the rotation operation in the second direction to the rotation operation in the first direction, the designated time is a time to resolve the time lag in the movement of the liquid contained in the multi-layer culture vessel to make the liquid collide with a side surface of the vessel.

2. The multi-layer culture vessel operational device according to claim 1, wherein each of the plurality of trays has a first side surface, a second side surface adjacent to the first side surface, a third side surface adjacent to the second side surface, and a fourth side surface adjacent to the third side surface, and wherein the control portion has a side surface adhering cell recovery function of operating the rotating portion so that a trypsin solution will collide with the first side surface, the second side surface, the third side surface, and the fourth side surface in the stated order.

3. The multi-layer culture vessel operational device according to claim 1 which is capable of receiving, from a cart movable with the multi-layer culture vessel including a plurality of trays mounted thereon, the multi-layer culture vessel and holding and rotating the multi-layer culture vessel, the multi-layer culture vessel operational device further comprising:

a shaking portion that is located below the rotating portion, is stored inside a body when not in use, and, when in use, protrudes to outside of the body, holds the multi-layer culture vessel, and performs a shaking operation of shaking the multi-layer culture vessel in a horizontal direction; and the control portion that controls operations of the shaking portion, wherein the control portion causes the shaking portion to perform the shaking operation following the rotation operation by the rotating portion, without returning the multi-layer culture vessel to the cart.

4. The multi-layer culture vessel operational device according to claim 3, wherein the control portion causes the shaking portion to receive the multi-layer culture vessel directly from the rotating portion, in the case of performing the shaking operation.

5. The multi-layer culture vessel operational device according to claim 3, wherein the rotating portion includes an electric motor, and is driven by electric power.

6. The multi-layer culture vessel operation device according to claim 1, wherein the control portion further has a function of introducing culture solution seeded with a cell into the multi culture vessel by causing the rotating portion to rotate the multi-layer culture vessel before performing the cell detachment process.

7. A multi-layer culture vessel operation method of operating a multi-layer culture vessel including a plurality of trays and in which a trypsin solution introduced, using the multi-layer culture vessel operational device according to claim 1, the multi-layer culture vessel operation method comprising stopping, while a cell detachment process is performed by causing the rotating portion to reciprocatingly swing the multi-layer culture vessel in the first direction and the second direction around the first rotation axis or the second rotation axis, movement of the multi-layer culture vessel for the designated time when switching from the rotation operation in the first direction to the rotation operation in the second direction and when switching from the rotation operation in the second direction to the rotation operation in the first direction.

8. The multi-layer culture vessel operation method according to claim 7, wherein each of the plurality of trays has a first side surface, a second side surface adjacent to the first side surface, a third side surface adjacent to the second side surface, and a fourth side surface adjacent to the third side surface, and wherein, after the cell detachment process, the rotating portion is operated so that the trypsin solution will collide with the first side surface, the second side surface, the third side surface, and the fourth side surface in the stated order.

9. The multi-layer culture vessel operation method according to claim 7, wherein, before the cell detachment process, introducing culture solution seeded with a cell into the culture vessel by causing the rotating portion to rotate the multi-layer culture vessel.

10. A multi-layer culture vessel operation system comprising:

a cart device movable with a multi-layer culture vessel including a plurality of trays mounted thereon; and the multi-layer culture vessel operational device according to claim 1 which capable of holding and rotating the multi-layer culture vessel, wherein the cart device includes:

a cart having wheels; and a fixing part that is removably mounted on the cart, and fixes the multi-layer culture vessel to the cart, wherein the multi-layer culture vessel operational device further comprises:

a shaking portion that holds the multi-layer culture vessel together with the fixing part, and performs a shaking operation of shaking the multi-layer culture vessel in a horizontal direction; and wherein the control portion controls operations of the shaking portion, and wherein the control portion causes the shaking portion to perform the shaking operation following the rotation operation by the rotating portion, without returning the multi-layer culture vessel to the cart.

11. The multi-layer culture vessel operation system according to claim 10, wherein the control portion causes the rotating portion to reciprocatingly swing the multi-layer culture vessel around the first rotation axis or the second rotation axis.

12. The multi-layer culture vessel operation system according to claim 10, wherein the shaking portion is capable of being stored inside a body of the operational device, and wherein the control portion causes the shaking portion to protrude from the body of the operational device when the shaking operation is performed.

13. The multi-layer culture vessel operation system according to claim 12, wherein the control portion causes the shaking portion to receive the multi-layer culture vessel together with the fixing part directly from the rotating portion, when the shaking operation is performed.

14. The multi-layer culture vessel operation system according to claim 10, wherein each of the rotating portion and the shaking portion includes an electric motor, and is driven by electric power.

15. The multi-layer culture vessel operation system according to claim 10, wherein the control portion controls the rotating portion to rotate the multi-layer culture vessel to introduce culture solution seeded with a cell into the culture vessel before the operations of the shaking portion.

16. A multi-layer culture vessel operation method of operating the multi-layer culture vessel including a plurality of trays using the operational device according to claim 3, the multi-layer culture vessel operation method comprising causing the shaking portion to perform the shaking operation following the rotation operation by the rotating portion.

* * * * *